United States Patent [19]
Kirwan, Jr.

[11] Patent Number: 5,290,285
[45] Date of Patent: Mar. 1, 1994

[54] ELECTROCAUTERY DEVICE HAVING TWO ELECTRICALLY ACTIVE AREAS OF THE TERMINAL END SPACED FROM EACH OTHER

[75] Inventor: Lawrence T. Kirwan, Jr., Kingston, Mass.

[73] Assignee: Kirwan Surgical Products, Inc., Rockland, Mass.

[21] Appl. No.: 872,333

[22] Filed: Apr. 23, 1992

[51] Int. Cl.$^5$ .............................................. A61B 17/39
[52] U.S. Cl. ........................................ 606/50; 606/48
[58] Field of Search ..................... 606/48, 50

[56] References Cited

U.S. PATENT DOCUMENTS

| | | | |
|---|---|---|---|
| 1,983,669 | 12/1934 | Kimble | 606/50 |
| 4,043,342 | 8/1977 | Morrison, Jr. | 606/50 |
| 4,548,207 | 10/1985 | Reimels | 606/50 |
| 4,674,499 | 6/1987 | Pao | 606/50 |
| 4,805,616 | 2/1989 | Pao | 606/50 |

OTHER PUBLICATIONS

Schmidt et al, "Vas Cautery ... Vasectomy", Urology, vol. III, No. 5, May 1974, pp. 604-605.

Primary Examiner—Lee S. Cohen

[57] ABSTRACT

This is an electrocautery device having an electrically active tip and an electrically active portion of the terminal end of the device spaced from the tip.

2 Claims, 1 Drawing Sheet

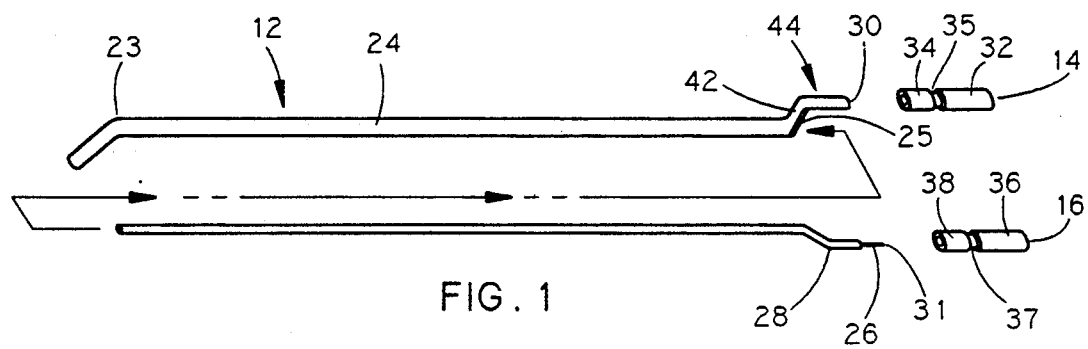
FIG. 1
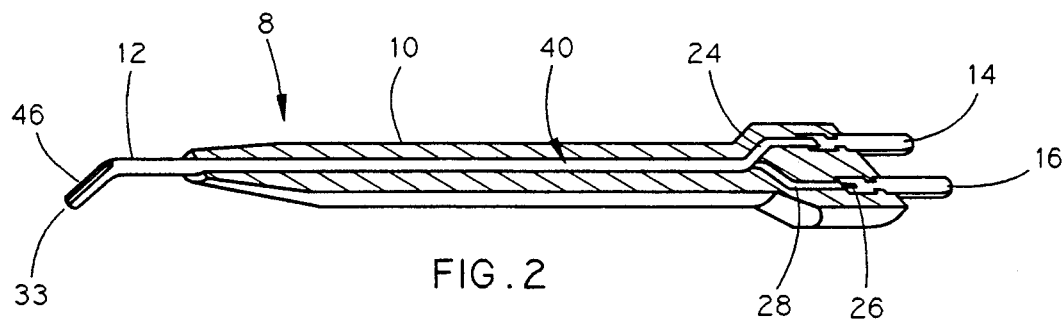
FIG. 2
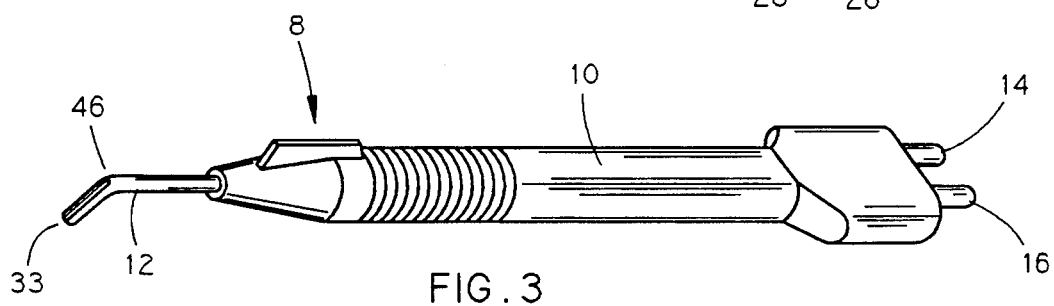
FIG. 3
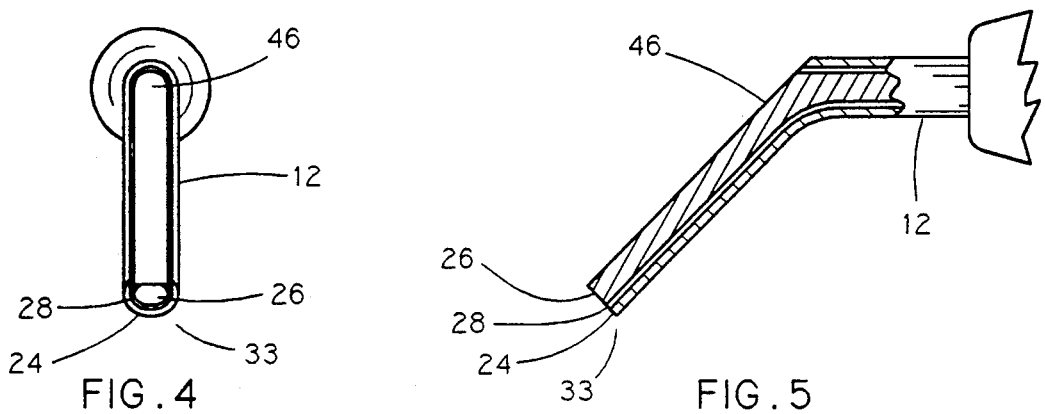
FIG. 4
FIG. 5

ELECTROCAUTERY DEVICE HAVING TWO ELECTRICALLY ACTIVE AREAS OF THE TERMINAL END SPACED FROM EACH OTHER

BACKGROUND OF THE INVENTION

1. Field of the Invention

This invention relates to an electrocautery device and more specifically to electrocautery devices having an electrically active tip and an electrically active portion of the terminal end spaced from the tip.

SUMMARY OF THE INVENTION

An electrically active wide stroke portion is formed by exposing the inner conductor from the elbow of the coaxial conductor to just above its terminal end, while maintaining the separation of the inner conductor and the outer conductor.

BRIEF DESCRIPTION OF THE DRAWINGS

Further details are explained below with the help of the example(s) illustrated in the attached drawings in which:

FIG. 1. is an exploded view of the electrocautery device showing the conductors and connector pins according to the present invention;

FIG. 2. is a cross sectional view of the electrocautery device showing the placement of the sub-assembly shown in FIG. 1 within the housing;

FIG. 3 is a perspective of the electrocautery device according to the present invention;

FIG. 4 is a sectional view of the first terminal end of the electrocautery device showing the position of the inner and outer conductors and the wide sweep portion; and FIG. 5 is a section partly in elevation according to the present invention.

DESCRIPTION OF THE PREFERRED EMBODIMENT(S)

The following specification includes a large part of the specification of U.S. Pat. No. 5,089,002 issued Feb. 18, 1992 to Lawrence T. Kirwan, Jr. The patentable difference between the present specification and U.S. Pat. No. 5,089,002 is that the present specification discloses two electrically active areas which can be used for operative purposes. There is shown in the drawings a electrocautery device 8 including an outer housing 10, a coaxial conductor 12, and first and second conductor pins 14, 16.

As shown in FIGS. 1 and 2, the coaxial conductor 12 comprises an outer conductor 24, an inner conductor 26 and a first terminal end 33.

The inner conductor 26 and the outer conductor 24 are separated for substantially their full length by an insulator 28. The outer conductor 24 comprises a length of stainless steel tubing with a first end 30 remote from the first terminal end 33. First and second bends 42, 44 are formed in the outer conductor 24 in opposed directions to each other, in close proximity to the first end 30 with the first bend 42 positioned further away from the first end 30 than the second bend 44. The first and second bends 42, 44 are formed at an angle to the longitudinal axis to outer conductor 24 and an aperture 25 is ground into the outer conductor 24 between the bends 42,44 as shown in FIG. 1. The inner conductor 26 comprises a length of stainless steel wire which includes a second end 31 separated from the the first terminal end 33.

As illustrated in FIG. 1, the coaxial conductor 12 may be formed by passing the terminal end, of the sub-assembly of the inner conductor 26 and the circumferential insulator 28, remote from the second end 31 through the aperture 25 and through the outer conductor 24. When the inner conductor 26 has been positioned within outer conductor 24 the second end 31, of the inner conductor 26, will be spaced from and in parallel relation to the first end 30 of the outer conductor 24. As illustrated in FIG. 4, the first terminal end 33 may be beveled by grinding it down to an angle or it may be left straight, conical or flat sided as required.

The first connector pin 14, which may be formed in one integral section from stainless steel wire, includes a body portion 32, an annular channel 35 and a sleeve portion 34. The body portion 32 is generally cylindrical while the sleeve portion 34 is tubular. Similarly, the second connector pin 16, may also be formed in one integral section from stainless steel wire, including a body portion 36, an annular channel 37 and a sleeve portion 38. As with the first connector pin 14, the body portion 36 of the second connector pin 16 is generally cylindrical while the sleeve portion 38 of the second connector pin 16 is tubular.

The first connector pin 14 is coupled to the outer conductor 24 by inserting the first end 30, of the outer conductor 24, into the sleeve portion 34. The sleeve portion 34 is crimped, fastening the first end 30 and the first connector pin 14 together. The second connector pin 16 is coupled to the outer conductor 24 by inserting the second end 31, of the outer conductor 24, into the sleeve portion 38. The sleeve portion 38 is crimped, fastening the second end 31 and the second connector pin 16 together. The assembly of the outer conductor 24, the inner conductor 26 with the connector pins 14, 16 forms an electrical sub-assembly 40. Both the inner conductor 26 and the outer conductor 24 are bent to provide an elbow 23 at the first terminal end 33 of the electrical sub-assembly 40. The outer conductor 24 is ground down from the elbow 23 to just above the terminal end 33 exposing the inner conductor 26 while maintaining the separation of the inner conductor 26 and the outer conductor 24 by the insulator 28 to form an electrically active wide stroke portion 46.

As illustrated in FIG. 3, the outer housing 10 is generally cylindrical in configuration and is formed in one unitary section over the sub-assembly 40 by placing a portion of the sub-assembly 40 in an injection mold and injecting a suitable plastic in a manner well known in the art. The molding operation leaves a portion of the first and second connector pins 14, 16 and a portion of the first terminal end 33 exposed. The outer housing 10, formed in this manner, electrically insulates the inner and outer conductor 26, 24 from accidental electrical shorting.

Electrically the outer conductor 24 may carry a positive current while the inner conductor 26 carries a negative current. The electrocautery device 8 is used for manipulating tissue during a medical operative procedure and at the surgeon's desire coagulating or desiccating the tissue by a voltage from an electrosurgical generator (not shown) connected to the electrocautery device 8. The surgeon may utilize the very end of the electrocautery device 8 to perform relatively small spot type operations or may use the wide stroke portion 46 in a wiping action to cover larger tissue areas. The electrosurgical generator is connected to the first and second connector pins 14, 16 by a standard socket assembly as is well known in the art.

What I claim is:

1. An electrocautery device including an outer housing, a coaxial conductor, and first and second conductor pins, the coaxial conductor having an outer conductor, an inner conductor, a first terminal end, and a second terminal end, the inner conductor and the outer conductor separated for substantially their full length by an insulator, the insulator removed from the inner conductor at the first terminal end, the outer conductor electrically connected to the first conductor pin at the second terminal end, the inner conductor electrically connected to the second conductor pin at the second terminal end, the first terminal end having an electrically active tip and an electrically active portion of the first terminal end spaced from the tip, the outer conductor, the inner conductor and the first and second conductor pins, forming a sub-assembly, the outer housing formed in one unitary section over the sub-assembly having opposite ends with the first and second conductor pins and the first terminal end extending from the opposite ends of the housing, first and second bends formed in the outer conductor in opposed direction to each other, in close proximity to the second terminal end with the first bend positioned further away from the second terminal end than the second bend.

2. An electrocautery device including an outer housing, coaxial conductor, and first and second conductor pins, the coaxial conductor having an outer conductor, an inner conductor, a first terminal end, and a second terminal end, the inner conductor and the outer conductor separated for substantially their full length by an insulator, the insulator removed from the inner conductor at the first terminal end, the second terminal end spaced from the first terminal end, the outer conductor electrically connected to the first conductor pin at the second terminal end, the inner conductor electrically connected to the second conductor pin at the second terminal end, the first terminal end having an electrically active tip and an electrically active portion of the first terminal end spaced from the tip, the outer conductor, the inner conductor and the first and second conductor pins, forming a sub-assembly, the outer housing formed in one unitary section over the sub-assembly having opposite ends with the first and second conductor pins and the first terminal end extending from the opposite ends of the housing, the coaxial conductor including an elbow portion, the elbow portion in close proximity to the first terminal end, a portion of the outer conductor of the coaxial conductor being removed from the elbow portion to just above the first terminal end exposing the inner conductor while maintaining the separation of the inner conductor and the outer conductor by the insulator to form an electrically active wide stroke portion.

* * * * *